United States Patent [19]

Brotzu et al.

[11] Patent Number: 5,201,778
[45] Date of Patent: Apr. 13, 1993

[54] VASCULAR PROSTHESIS CONTAINING IN THE WALL MICROCAPSULES, INCLUDING HORMONE-PRODUCING CELLS

[75] Inventors: Giovanni Brotzu, Piazza Garibaldi, 4, 09134 Cagliari; Riccardo Calafiore, Perugia, both of Italy

[73] Assignee: Giovanni Brotzu, Cagliari, Italy

[21] Appl. No.: 820,006

[22] Filed: Jan. 13, 1992

Related U.S. Application Data

[62] Division of Ser. No. 548,372, Jul. 5, 1990, Pat. No. 5,104,403.

[30] Foreign Application Priority Data

Jul. 4, 1989 [IT] Italy ............................... 21086 A/89

[51] Int. Cl.⁵ ............................................... A61F 2/06
[52] U.S. Cl. ........................................... 623/66; 623/1
[58] Field of Search .......................... 623/1, 11, 12, 66; 424/422, 423

[56] References Cited

U.S. PATENT DOCUMENTS

| 4,309,776 | 1/1982 | Berguer | 623/1 |
| 4,409,331 | 10/1983 | Lim | 435/178 |
| 5,104,403 | 4/1992 | Brotzu et al. | 623/1 |

FOREIGN PATENT DOCUMENTS

| 0188309 | 7/1986 | European Pat. Off. | 623/11 |
| 0393788 | 10/1990 | European Pat. Off. | 623/1 |

Primary Examiner—David Isabella
Assistant Examiner—Debra S. Brittingham
Attorney, Agent, or Firm—Birch, Stewart, Kolasch & Birch

[57] ABSTRACT

A vascular prosthesis having a low porosity outer material such as PTFE, and an inner synthetic tubular mesh. Semi-permeable microcapsules that contain hormone-producing cells, are placed between the outer material and the inner mesh. The microcapsules are preferably made of polysaccharides or amino-acid polymers.

5 Claims, 1 Drawing Sheet

VASCULAR PROSTHESIS CONTAINING IN THE WALL MICROCAPSULES, INCLUDING HORMONE-PRODUCING CELLS

This application is a divisional of copending application Ser. No. 07/548,372 filed on Jul. 5, 1990, now U.S. Pat. No. 5,104,403. The entire contents of which are hereby incorporated by reference.

BACKGROUND OF THE INVENTION

1. Field of the Invention

The present invention relates to vascular prostheses that contain hormone-producing cells in microcapsule form.

2. Description of Related Art

Microcapsules consisting of saccharide, amino-acid polymers and other materials, such as agarose polymers, are already known and are apt to contain living hormone-producing cells.

Microcapsules with the above-mentioned features are manufactured and marketed by Damon, Biotech of Boston under the name of Encapcell, and also by other laboratories.

These microcapsules allow for the protection of the cells contained inside the microcapsules against a possible rejection phenomena, while allowing the metabolic activity of the cells to continue and permit the leaking out of the hormones secreted by the cells.

However, the introduction of such microcapsules in the body brings about some problems, among which the following should be emphasized:

1) the microcapsules introduced in the body are wrapped in a reactive connective tissue, which prevents both the metabolic supply to the cells and the leaking out of the secreted hormones;

2) the microcapsules, if injected into a cavity such as the peritoneal cavity, tend to move downwards and concentrate in a limited area, thus causing a lively connective reaction involving them.

SUMMARY OF THE INVENTION

The problems of the prior technique can be solved through the use of a vascular prosthesis of a low porosity material, such as PTFE inside of which is another prosthesis of a synthetic tubular mesh which allows for oxygen and hormones to pass through microcapsules of semi-permeable materials, such as; polysaccharides and amino-acid polymers or, that contain the hormone-producing cells, are placed between the two prostheses. The preparation of the vascular prosthesis involves the following steps:

a) Inside of a vascular prosthesis of a low posity mesh such as PTFE a second prosthesis is placed, made of a synthetic tubular mesh with external support (EXS);

b) the microcapsules which consist of, for example saccharide or amino-acid polymers and contain the hormone-producing cells are placed in the space between the two prosthesis and;

c) a spindle of a plastic material is then introduced into the interior of the prosthesis.

Prostheses according to the present invention are used to create artervenous fistulas.

DETAILED DESCRIPTION OF THE INVENTION

Figure 1:
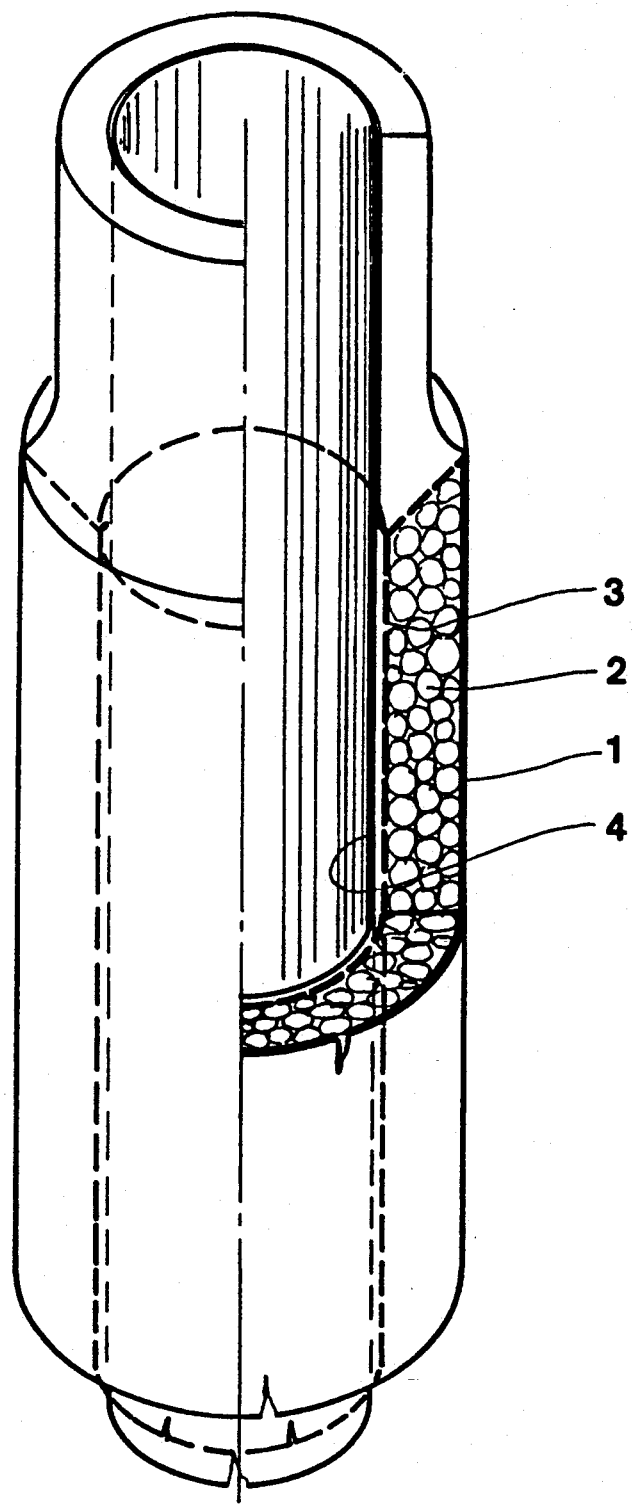

The characteristics and advantages of the vascular prostheses and the relative preparation process, according to the present invention, will be dealt with in greater detail in the following description, also referring to the enclosed FIG. 1.

FIG. 1 represents schematically the prosthesis according to the present invention. With reference to the symbols of said figure, microcapsules 2, containing the hormone-producing cells, are placed between a prosthesis 1 of PTFE or of a low porosity material and a prosthesis 3 of a synthetic tubular mesh, and in said prosthesis 3 a plastic material spindle 4 is introduced.

The tubular mesh is preferably made of polyester or polytetrafluoroethylene fibers (for example, Dacron or Teflon fibers) and has an internal diameter of between 4 and 14 mm with an external support (EXS).

The empty spaces between the filaments making up such mesh are between 10 and 300 micron such that is such the microcapsules are retained.

The microcapsules are made of saccharide and amino-acid polymers or other semi-permeable material with a porosity of about 60.000 Dalton. This allows for the transfer of the metabolic products from the inside to the outside and viceversa, but not the passage of the immunoglobulins or other high molecular weight molecules.

The spindle is preferably made of silastic or PVC and has an external diameter compatible with the internal diameter of prosthesis 3. The spindle transforms the space between prosthesis 1 and prosthesis 3, in which the microcapsules 2 will be placed, into a virtual space. The prosthesis according to the present invention is implanted, after extraction of the spindle into the recipient through an artero-venous fistula.

A vascular prosthesis is thus obtained; consisting inside of a synthetic tubular mesh that retains the microcapsules, which are in practice exposed to the hematic flow and which is covered by an endothelium-like tissue.

In such vascular prosthesis the hematic flow allows for the metabolism of the cells contained in the microcapsules to exist and at the same time it also allows for the circulation of the hormones secreted by the cells themselves.

A particularly useful application is possible when the microcapsules contain Langherans islands cells which secrete insulin.

We claim:

1. A process for the preparation of a vascular prosthesis comprising:

forming an outer material having a low porosity and an inner tubular porous mesh of synthetic material said porous mesh having a porosity to allow oxygen and hormones to pass therethrough; disposing microcapsules between said outer material and said inner tubular mesh, said microcapsules being made of a semi-permeable material and containing hormone-producing cells; and introducing into said prosthesis a spindle of plastic material sized to be introduced into said prosthesis.

2. Process according to claim 1, wherein said spindle is made of a material selected from the group consisting of silastic and PVC and has an external diameter compatible with the internal diameter of said mesh.

3. Process according to claim 1, wherein said mesh is made up of fibers selected from the group consisting of polyester and polytetrafluoroethylene fibers.

4. Process according to claim 1, wherein said tubular mesh has an internal diameter of between 4 and 14 mm.

5. Process according to claim 1, wherein free spaces between filaments making up said mesh are of between 10 and 300 microns.

* * * * *